(12) United States Patent
Ostrov et al.

(10) Patent No.: US 8,501,242 B2
(45) Date of Patent: Aug. 6, 2013

(54) METHODS AND COMPOSITIONS FOR TREATING NEOPLASIA

(75) Inventors: David A. Ostrov, Gainesville, FL (US); Carmen J. Allegra, Gainesville, FL (US)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 13/322,842

(22) PCT Filed: May 29, 2010

(86) PCT No.: PCT/US2010/036778
§ 371 (c)(1),
(2), (4) Date: Mar. 7, 2012

(87) PCT Pub. No.: WO2010/138955
PCT Pub. Date: Dec. 2, 2010

(65) Prior Publication Data
US 2012/0156212 A1 Jun. 21, 2012

Related U.S. Application Data

(60) Provisional application No. 61/182,592, filed on May 29, 2009.

(51) Int. Cl.
| | | |
|---|---|---|
| A61K 35/12 | (2006.01) | |
| A61K 31/198 | (2006.01) | |
| A61K 31/70 | (2006.01) | |
| A61K 31/505 | (2006.01) | |

(52) U.S. Cl.
USPC .... 424/573; 435/6.14; 424/155.1; 424/174.1; 424/141.1; 514/129; 514/252.12; 514/274; 514/345; 514/562; 562/430; 562/456; 562/557; 562/594

(58) Field of Classification Search
USPC ......... 424/573, 155.1, 174.1, 141.1; 435/573; 514/129, 252.12, 274, 345, 562; 562/430, 562/456, 567, 594
See application file for complete search history.

(56) References Cited

U.S. PATENT DOCUMENTS

| | | | |
|---|---|---|---|
| 5,614,505 | A | 3/1997 | Gmeiner et al. |
| 5,661,155 | A | 8/1997 | Pendergast et al. |
| 6,537,999 | B2 | 3/2003 | Gangjee |
| 6,569,634 | B1 | 5/2003 | Hoshino et al. |

(Continued)

FOREIGN PATENT DOCUMENTS

| | | |
|---|---|---|
| CA | 2333145 C | 3/2008 |
| WO | WO-0009131 A1 | 2/2000 |

(Continued)

OTHER PUBLICATIONS

Gura, Systems for identifying new drugs are often faulty, Science, Nov. 7, 1997; 278, pp. 1041-1104.*

(Continued)

*Primary Examiner* — Savitha Rao
(74) *Attorney, Agent, or Firm* — Edwards Wildman Palmer LLP; Peter F. Corless; Jeffrey D. Hsi

(57) ABSTRACT

The present invention relates to compounds as novel thymidylate synthase inhibitors, novel strategies to treat or prevent neoplasia in a subject, methods and compositions thereof.

10 Claims, 3 Drawing Sheets

U.S. PATENT DOCUMENTS

| | | |
|---|---|---|
| 6,794,370 B2 | 9/2004 | Achterrath |
| 7,199,232 B2 | 4/2007 | Glaab et al. |
| 7,345,039 B2 | 3/2008 | Redmond et al. |
| 2002/0137748 A1* | 9/2002 | Smith et al. .......... 514/251 |
| 2006/0051764 A1 | 3/2006 | Mandola et al. |
| 2008/0026415 A1 | 1/2008 | Rimm et al. |
| 2008/0032948 A1 | 2/2008 | Niyikiza et al. |
| 2008/0045451 A1 | 2/2008 | Loeb et al. |

FOREIGN PATENT DOCUMENTS

| | | |
|---|---|---|
| WO | WO-2006094406 A1 | 9/2006 |
| WO | WO-2006087756 A3 | 11/2006 |
| WO | WO-2006124684 A3 | 4/2007 |
| WO | WO-2005076984 A3 | 4/2009 |

OTHER PUBLICATIONS

Booth, Oncology's trials, Nature Reviews Drug Discovery, vol. 2, Aug. 2003, 609-611.*

Papamichael (The Oncologist, 1999, vol. 4; pp. 478-487).*

Y Ix, A Formentini, G. Nakajima, M. Kornmann, J. Ju; Validation of Biomarkers Associated With 5-Fluorouracil and Thymidylate Synthase in Colorectal Cancer; Oncol Rep. Jan. 2008; 19(1):257-62.

L. Pare, E. Marcuello, A. Altes, E. De Rio, L. Sedano, A. Barnadas, M. Baiget; Transcription Factor-Binding Sites in the Thymidylate Synthase Gene: Predictors of Outcome in Patients with Metastatic Colorectal Cancer Treated with 5-Fluorouracil and Oxaliplatin; The Pharmacogenomics Journal Oct. 2008;8(5):315-20, Epub Aug. 7, 2007.

SA Jensen, B Vainer, JB Sorensen, The Prognostic Significance of Thymidylate Synthase and Dihydropyrimidine Dehydrogenase in Colorectal Cancer of 303 Patients Adjuvantly Treated with 5-Fluorouracil; Int. J Cancer Feb. 1, 2007;120(3):694-701.

Yaguang Xi, Go Nakajima, John C. Schmitz, Edward Chu. Jingfang Ju; Multi-Level Gene Expression Profiles Affected by Thymidylate Synthase and 5-Fluorouracil in Colon Cancer; BMC Genomics 2006, 7:68.

NL Lehman, Future Potential of Thymidylate Synthase Inhibitors in Cancer Therapy; Expert Opin Investig Drugs. Dec. 2002;11(12):1775-87.

* cited by examiner

METHODS AND COMPOSITIONS FOR TREATING NEOPLASIA

RELATED APPLICATIONS

This application is a U.S. National stage application of PCT International Application PCT/US2010/036778, filed May 29, 2010, which claims the benefit of U.S. Provisional Patent Application No. 61/182,592, filed May 29, 2009, the contents of which are incorporated herein by reference in their entirety.

BACKGROUND OF THE INVENTION

Neoplasia (i.e. cancer) is a class of diseases which affect people at all ages, even fetuses, but the risk for most varieties increases with age. Cancer causes about 13% of all deaths. According to the American Cancer Society, 7.6 million people died from cancer in the world during 2007.

Thymidylate synthase (also called "thymidylate synthetase") is the enzyme used to generate thymidine monophosphate, which is subsequently phosphorylated to thymidine triphosphate for use in DNA synthesis and repair. Deoxyuridine monophosphate (dUMP) and N5,N10-methylene tetrahydrofolate are together used to form deoxy thymidine monophosphate, by reductive methylation, yielding dihydrofolate as a secondary product. Human thymidylate synthase is a key enzyme in DNA synthesis, often overexpressed in cancer cells.

Human thymidylate synthase has been a long-standing focus as a validated target for cancer therapy. Existing cancer chemotherapies have utilized anti-cancer agents such as fluorinated pyrimidine fluorouracil, or folate analogues to inhibit thymidylate synthetase. One of such chemotherapeutic agents is Raltitrexed (trade name Tomudex). Another example is 5-Fluorouracil.

Despite the fact that human thymidylate synthetase has been of longstanding interest as a target for cancer chemotherapeutic agents, there is a limited range of options available in the clinic. Certain existing anti-cancer drugs have profiles of adverse effects. For example, adverse effects are reported in connection with the use of 5-Fluorouracil in chemotherapy. Side effects include myelosuppression, mucositis, dermatitis, diarrhea and cardiac toxicity. Furthermore, there is a metabolism problem in connection with the use of 5-Fluorouracil in individuals.

In recent years, cancer immunotherapy has been established as a viable approach to treat neoplasia in a subject. Cancer immunotherapy is a therapeutic strategy which is designed to induce a subject's own immune system to fight the tumor. Contemporary methods for generating an immune response against tumors include intravesical BCG immunotherapy for superficial bladder cancer, and use of interferons and other cytokines to induce an immune response in renal cell carcinoma and melanoma subjects. There is, however, a gap in that both strategies have not been directed at a specific validated target for cancer therapeutics using an individualized approach.

Therefore, there is an urgent need for improved strategies to treat or prevent neoplasia in a subject.

SUMMARY OF THE INVENTION

The present invention provides compounds, and methods of using such compounds for treating a subject suffering from or susceptible to neoplasia (i.e. cancer).

In particular, the present invention provides compounds capable of inhibiting the activities of thymidylate synthase by modulating (or interfering with) association among thymidylate synthase monomers. In particular, the compounds are capable of interfering with dimerization between the thymidylate synthase monomers. Certain embodiments of the invention include, but not limited to, a compound selected from the group consisting of (3,5-diiodo-4-oxo-1(4H)-pyridinyl)acetic acid ("NSC60718"), P-(diethylsulfamoyl)benzoic acid ("NSC49467"), 3-(acetylamino)-2,4,6-triiodobenzoic acid, 6-(methylamino)hexane-1,2,3,4,5-pentol ("NSC141235"), 2-acetamido-3-sulfanylpropanoic acid ("NSC111180"), piperazine. 2,3-dihydroxysuccinate ("NSC86777"), 1-ethyl-4-oxo-1,4-dihydro[1,3]-dioxolo[4,5-g]cinnoline-3-carboxylic acid ("NSC304467"), 2,3-dihydroxypropyl dihydrogen phosphate ("NSC9231"), and 2,3-dimercaptosuccinic acid ("NSC16867"), and salts (including pharmaceutically acceptable salts), solvates and hydrates thereof.

One aspect of the present invention is directed to a method of treating or preventing neoplasia in a subject. The method includes administering to said subject an effective amount of a compound, wherein said compound has inhibitory activity against thymidylate synthase by interfering with association among thymidylate synthase monomers. The method also includes administering to a subject a therapeutically effective amount of salt, hydrate or solvate of the afore-mentioned compounds.

In certain embodiments, the compound administered to the subject is capable of interfering with dimerization between thymidylate synthase monomers. In another embodiment, the method comprises administering to the subject an additional therapeutic agent. In certain embodiments, the additional therapeutic agent is selected from the group consisting of fluorinated pyrimidine fluorouracils and folate analogues. In one embodiment, the additional therapeutic agent is 5-fluorouracil ("5-FU").

In one embodiment, the compound of the present application and the additional therapeutic agent are administered simultaneously. In another embodiment, the compound and the additional therapeutic agent are administered sequentially.

In one embodiment, the method also includes treating the subject with an additional cancer treatment. In certain embodiments, the additional cancer treatment is selected from the group of surgery, chemotherapy, radiation therapy, immunotherapy and monoclonal antibody therapy. A particular example is that the additional cancer treatment is an immunotherapy. In one embodiment, the immunotherapy is an individualized immunotherapy. Certain embodiments provide that the immunotherapy is designed based on generation of tumor antigen specific T lymphocytes in the subject.

Another aspect of the present invention is directed to a method of identifying a compound for treating or preventing neoplasia in a subject, whereas the compound is capable of modulating (or interfering with) association among thymidylate synthase monomers. The method comprises: a) obtaining thymidylate synthases, wherein the thymidylate synthases comprise monomers; and b) evaluating inhibitory activity of the compound against the thymidylate synthases.

In one embodiment, the method further includes evaluating inhibitory activity of a mixture against the thymidylate synthases, wherein the mixture consists essentially of the compound being evaluated and an additional anti-cancer agent. In certain embodiments, the method further includes determining whether the compound has a non-competitive or competitive inhibitory activity against the thymidylate synthase by comparing the inhibitory activity of the compound with the inhibitory activity of the mixture.

In one aspect, a kit for treating or preventing neoplasia in a subject is provided and includes a compound herein, or pharmaceutically acceptable esters, salts, and prodrugs thereof, and instructions for use of the kit. In one embodiment, the kit further includes an additional therapeutic agent. Certain embodiments provide that the additional therapeutic agent is selected from the group consisting of fluorinated pyrimidine fluorouracils and folate analogues.

In another aspect, the invention provides a packaged composition including an effective amount of a compound capable of modulating (or interfering with) association among the thymidylate synthase monomers, and a pharmaceutically acceptable carrier or diluent. The composition may be formulated for treating a subject suffering from or susceptible to neoplasia, and packaged with instructions to treat a subject suffering from or susceptible to neoplasia.

One aspect of the present invention provides a pharmaceutical composition for treating or preventing neoplasia in a subject, wherein the pharmaceutical composition comprises an effective amount of a compound capable of modulating or interfering with association among the thymidylate synthase monomers.

One embodiment provides that the compound is capable of interfering with dimerization between the thymidylate synthase monomers. In another embodiment, the compound is identified as capable of interfering with dimerization between the thymidylate synthase monomers. Some embodiments provide that the pharmaceutical composition further comprises an additional therapeutic agent selected from the group consisting of fluorinated pyrimidine fluorouracils and folate analogues. In one embodiment, the additional therapeutic agent is 5-Fluorouracil.

One embodiment provides that the compound of the present invention is acylcysteine, or a pharmaceutically acceptable salt, solvate, clathrate, hydrate, polymorph, or prodrug thereof.

In another aspect, the invention provides a Use of a compound capable of interfering with or modulating association among thymidylate synthases for the manufacture of a medicament for the treatment or prevention of neoplasia in a subject.

The invention also provides methods for designing, evaluating and identifying compounds which bind to binding pockets of the thymidylate synthase. The method includes separating or obtaining the thymidylate synthase monomers. Certain embodiments include identifying a binding pocket in the thymidylate synthase for association among the monomers. The compounds designed or identified are capable of modulating or interfering with association among thymidylate synthase monomers. Other embodiments of the invention are disclosed infra.

BRIEF DESCRIPTION OF THE DRAWINGS

The present invention is further described below with reference to the following non-limiting examples and with reference to the following figures, in which.

DETAILED DESCRIPTION OF THE INVENTION

Figure 1:
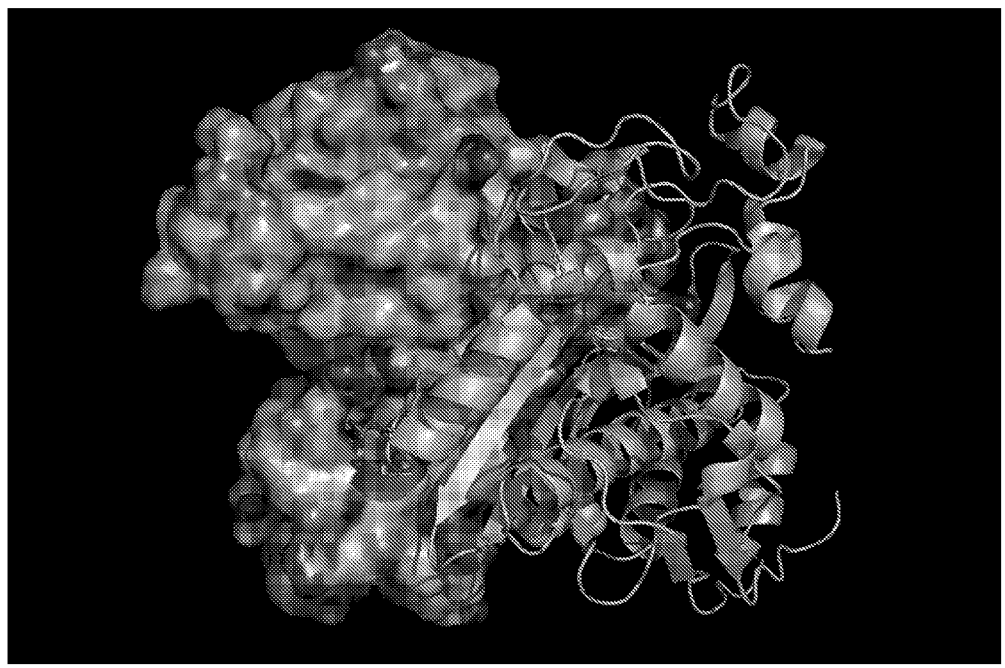
FIG. 1 depicts the crystal structure of human thymidylate synthase.
Figure 2:
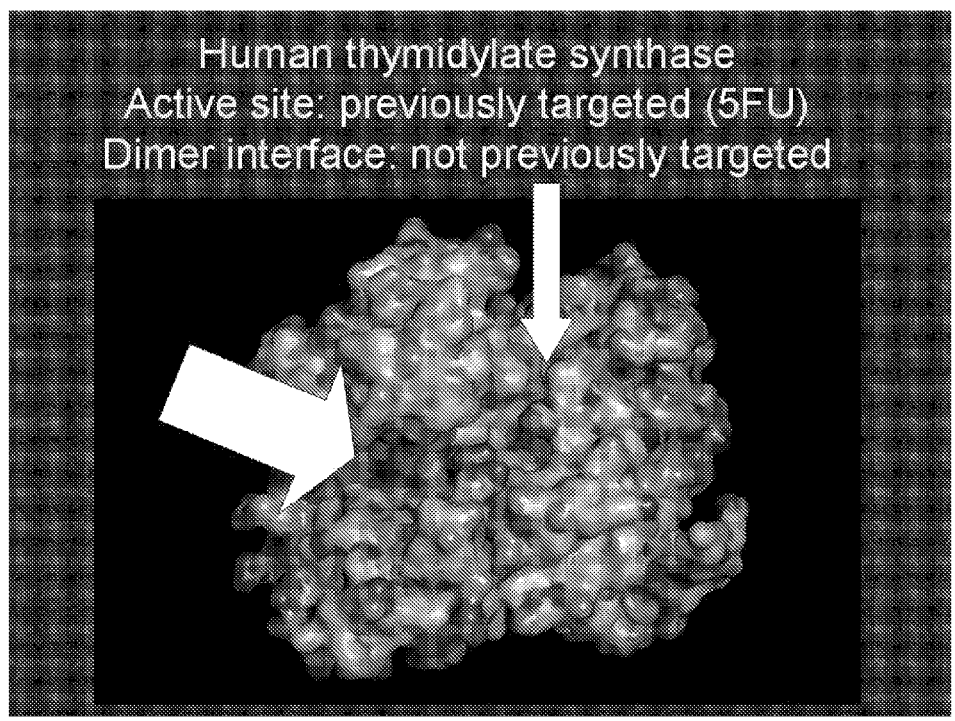
FIG. 2 shows dimer interfaces (arrowed) in the crystal structure of human thymidylate synthase.
Figure 3:
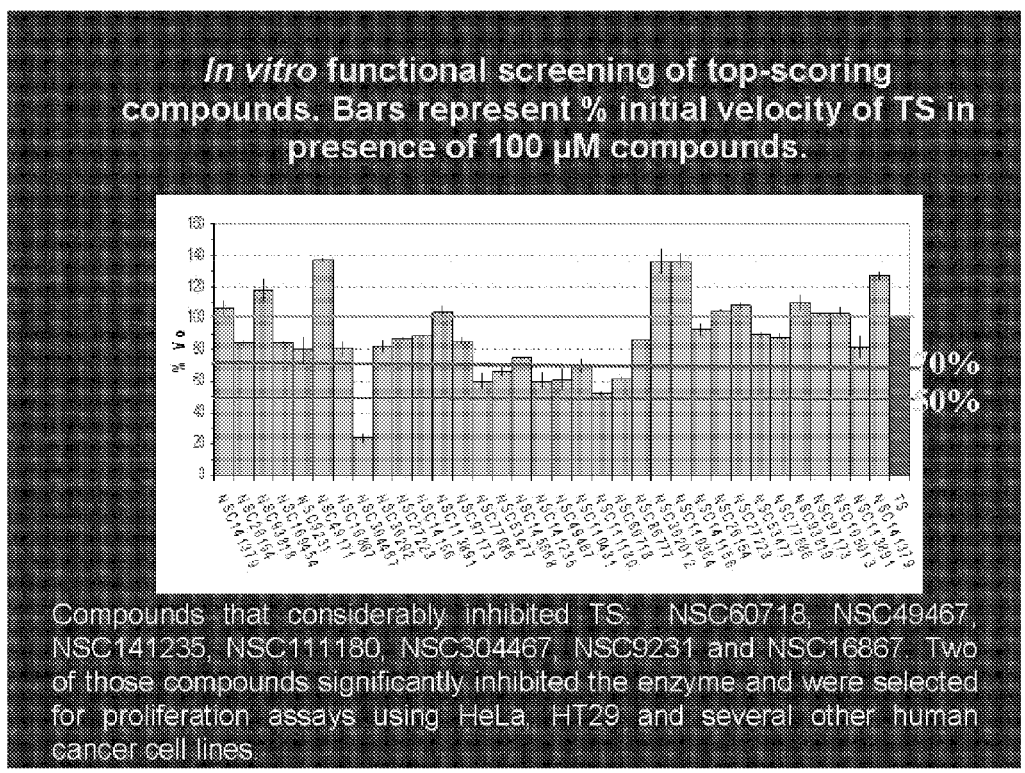
FIG. 3 presents results from in vitro functional screening of the compounds.

The present invention provides compounds for treating or preventing neoplasia in a subject, compositions and methods of use thereof. The compounds have inhibitory activities against the thymidylate synthase through modulating or interfering with association among the enzymes. In particular, the compounds of the present invention are capable of modulating or interfering with dimerization between the thymidylate synthase monomers.

Thymidylate synthase (also called "thymidylate synthetase") is the enzyme used to generate thymidine monophosphate, which is subsequently phosphorylated to thymidine triphosphate for use in DNA synthesis and repair. Deoxyuridine monophosphate (dUMP) and N5,N10-methylene tetrahydrofolate are together used to form deoxy thymidine monophosphate, by reductive methylation, yielding dihydrofolate as a secondary product. Human thymidylate synthase is a key enzyme in DNA synthesis, often overexpressed in cancer cells.

Existing chemotherapeutic agents used in cancer treatments are found to inhibit human thymidylate synthase by interacting directly with the active site of the enzyme. It has also been found that human thymidylate synthase is most catalytically active in a homodimeric form, as characterized by x-ray crystallography and other methods.

The present inventors have discovered that human thymidylate synthase exists in monomer form. The present inventors have separated and obtained the monomers of human thymidylate synthases. Further, the present inventors have evaluated the protein-protein interface in human thymidylate synthase subunits and have identified a binding site in the enzyme. The binding site is expected to play a role when the human thymidylate synthase subunits associate with each other. The present inventors have discovered that drugs targeting the binding site interfere with dimerization and activity of the human thymidylate synthase. Further, the present inventors have found that this targeted binding site (i.e. structural pocket) is outside the conventional active site of human thymidylate synthase.

Approximately 140,000 small molecule compounds have been screened for their abilities to interact with the aforementioned structural pocket based on the coordinates derived from the crystal structure. The present inventors have also tested compounds for their ability to inhibit human thymidylate synthase through this novel, non-conventional mechanism. The present inventors have now identified compounds that are inhibitory against human thymidylate synthase through a non-competitive enzyme mechanism, that is, these compounds inhibit human thymidylate synthase outside the conventional active site. In particular, it is believed that the compounds inhibit human thymidylate synthase through interfering with association (e.g. dimerization) among monomers of human thymidylate synthase.

Furthermore, recent developments on cancer treatments include cancer immunotherapy as a viable approach to treat neoplasia in a subject. Contemporary methods for generating an immune response against tumors include intravesical BCG immunotherapy for superficial bladder cancer, and use of interferons and other cytokines to induce an immune response in renal cell carcinoma and melanoma subjects.

There have been important recent advances in eliciting tumor specific immune responses and in the ability to target the function of key proteins involved in tumor survival. For example, recent research has intensively focused on developing vaccines to generate specific immune responses for a number of tumors, for example, malignant melanoma and renal cell carcinoma. Methods have also been established to elicit T cell responses specific for human thymidylate synthase. It has been demonstrated that methods have been established to generate class I and class II Human Leukocyte Antigen restrict T cell responses to tumor antigens both in vitro and in vivo. Nevertheless, these studies have focused on single, well characterized Human Leukocyte Antigens, such as Human Leukocyte Antigen A2. This strategy has not made it feasible for an individualized immunotherapy for the general population expressing different Human Leukocyte Antigens.

The present inventors have selected subject specific peptides based on the Human Leukocyte Antigens expressed by a subject. These peptides are capable of interacting with the Human Leukocyte Antigen A molecules expressed on a diverse set of cancer cell types. The well characterized peptide binding motifs are used for Human Leukocyte Antigen A molecules to select peptides derived from human thymidylate synthase to be used to stimulate T lymphocytes isolated from peripheral blood mononuclear cells. Based on the tests, a rapid and economical protocol is formulated to stimulate tumor specific T cells in an individually optimized manner and boost the adaptive immune response.

Therefore, the present invention also provides novel strategies for treating or preventing neoplasia in a subject. The strategies comprise administering to the subject a compound of the present invention and/or an additional cancer treatment. A particular example of such additional cancer treatment includes treating the subject with an immunotherapy, wherein the immunotherapy is individualized, based on the generation of tumor antigen specific T lymphocytes.

Another aspect of the present invention is directed to a method of identifying a compound for treating or preventing neoplasia in a subject, whereas the compound is capable of modulating (or interfering with) association among thymidylate synthase monomers. In one embodiment, the compound is identified as capable of modulating (or interfering with) association among thymidylate synthase monomers. The method comprises: a) separating or obtaining thymidylate synthase monomers; and b) evaluating inhibitory activity of the compound against the thymidylate synthase. Certain embodiments provide a method further including evaluating inhibitory activity of a mixture against the thymidylate synthase, wherein the mixture consists essentially of the compound being evaluated and an additional anti-cancer agent, and/or determining whether the compound has a non-competitive or competitive inhibitory activity against the thymidylate synthase by comparing the inhibitory activity of the compound with the inhibitory activity of the mixture.

In one aspect, a kit for treating or preventing neoplasia in a subject is provided. The kit includes a compound of the present invention or pharmaceutically acceptable esters, salts, hydrates, solvates and prodrugs thereof, and instructions for use of the kit.

In another aspect, the invention provides a packaged composition including an effective amount of a compound capable of modulating (or interfering with) association among the thymidylate synthase monomers, and a pharmaceutically acceptable carrier or diluent. The composition may be formulated for treating a subject suffered from or susceptible to neoplasia, and packaged with instructions for such uses.

One aspect of the present invention provides a pharmaceutical composition for treating or preventing neoplasia in a subject, wherein the pharmaceutical composition comprises an effective amount of a compound capable of modulating or interfering with association among the thymidylate synthase monomers. In one embodiment, the compound is identified as capable of modulating (or interfering with) association among thymidylate synthase monomers.

1. DEFINITIONS

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain or branched-chain alkyl groups. The term "alkyl" further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer.

The term "cycloalkyl" refers to the radical of saturated or unsaturated cyclic alkyl groups. In preferred embodiments, a cycloalkyl group has from 3-10 carbon atoms in its ring structure, and more preferably have 3, 4, 5, 6 or 7 carbons in the ring structure.

Moreover, the term "alkyl" as used throughout the specification and sentences are intended to include both "unsubstituted alkyl" and "substituted alkyl," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Similarly, Cycloalkyls can be also substituted, e.g., with the substituents described above. An "alkylaryl" moiety is an alkyl substituted with an aryl (e.g., phenylmethyl(benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a disorder delineated herein. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight. Certain examples are about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The terms "halogen" and "halo" designate —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a compound inhibit activity of a target in response to exposure to a compound of the invention, including for example in an subject (e.g., animal, human) such that a desired end result is achieved, e.g., a therapeutic result.

The term "obtaining" as in "obtaining a compound capable of modulating (agonizing, antagonizing) a target delineated herein and is intended to include purchasing, synthesizing or otherwise acquiring the compound.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "neoplasia" or "cancer" refers to a class of diseases in which a group of cells display uncontrolled growth (division beyond the normal limits), invasion (intrusion on and destruction of adjacent tissues), and sometimes metastasis (spread to other locations in the body via lymph or blood). The term intends to include all types of cancers having been diagnosed or to be diagnosed, including but not limited to, breast cancer, bladder cancer, colon and rectal cancer, colorectal cancer, cutaneous melanoma, endometrial cancer, kidney cancer, lung cancer, ovarian cancer, pancreatic cancer, prostate cancer, non-Hodgkin lymphoma, leukemia, skin cancer, thyroid cancer, gastrointestinal cancer, and head and neck cancer.

The term of "chemotherapy" refers to treatment of disease by chemicals that kill cells, specifically those of micro-organisms or cancer.

The language "a prophylactically effective amount" of a compound refers to an amount of a compound of the invention any formula herein or otherwise described herein which is effective, upon single or multiple dose administration to the subject, in preventing or treating a disorder herein.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from neoplasia herein or who could otherwise benefit from the administration of a compound of the invention of the invention, such as human and non-human animals. Preferred humans include human patients suffering from or prone to suffering from neoplasia, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to neoplasia (or a cancer)" is meant to include subjects at risk of developing a cancer, e.g., including those delineated herein, i.e., subjects suffering from a cancer or symptom thereof, subjects having a family or medical history of a cancer or symptom thereof, and the like.

The phrases "systemic administration," "administered systemically", "peripheral administration" and "administered peripherally" as used herein mean the administration of a compound of the invention(s), drug or other material, such that it enters the subject's system and, thus, is subject to metabolism and other like processes, for example, subcutaneous administration.

The language "therapeutically effective amount" of a compound of the invention of the invention refers to an amount of an agent which is effective, upon single or multiple dose administration to the subject, treating or preventing cancer, or in prolonging the survivability of the subject with a cancer beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. COMPOUNDS OF THE INVENTION

The compounds of the present invention demonstrate inhibitory activity against the thymidylate synthase. In one embodiment, the compound is capable of modulating or interfering with association among the thymidylate synthase monomers. In particular, the compound is capable of modulating or interfering with dimerization between thymidylate synthase monomers. In another embodiment, the compound is capable of modulating or interfering with translocation of thymidylate synthase, or fragments or monomers thereof. In other embodiments, the compounds are identified as having the aforementioned activity. The compounds of the present invention also relate to the pharmaceutically acceptable salts, esters, hydrates, solvates, clathrates, polymorphs, and prodrugs of the above-mentioned compounds. Without wishing to be bound by any theory, the compounds of the present invention are discovered to be thymidylate synthase inhibitors.

In one embodiment, the compound of the present invention is acylcysteine or a pharmaceutically acceptable salt, solvate, clathrate, hydrate, polymorph, or prodrug thereof.

In another embodiment, the compounds are any of the following, or derivatives (i.e., substituted compounds) thereof:

1) NSC60718: (3,5-diiodo-4-oxo-1(4H)-pyridinyl)acetic acid:

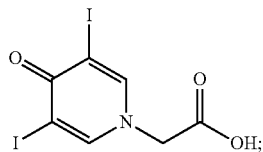 [SMILES: O=C(O)Cn1cc(I)c(=O)c(I)c1]

2) NSC49467: P-(Diethylsulfamoyl)benzoic acid:

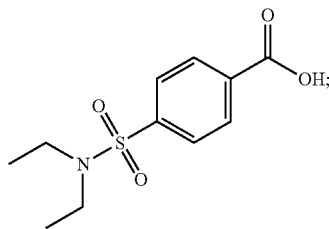 [SMILES: CCN(CC)S(=O)(=O)c1ccc(C(=O)O)cc1]

3) NSC141235: 3-(acetylamino)-2,4,6-triiodobenzoic acid.6-(methylamino)hexane-1,2,3,4,5-pentol:

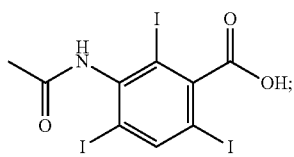

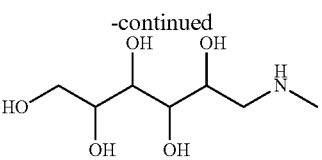

4) NSC 111180: 2-acetamido-3-sulfanylpropanoic acid:

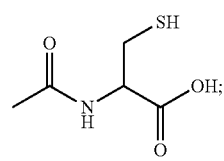

5) NSC86777: piperazine. 2,3-dihydroxysuccinate:

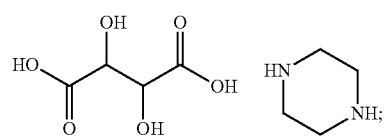 [SMILES: O=C(O)C(O)C(O)C(=O)O ; C1CNCCN1]

6) NSC304467: 1-Ethyl-4-oxo-1,4-dihydro[1,3]dioxolo[4,5-g]cinnoline-3-carboxylic acid:

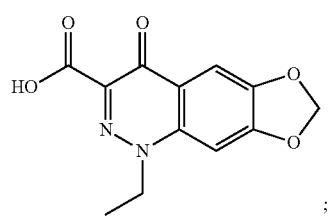 [SMILES: CCn1nc(C(=O)O)c(=O)c2cc3c(cc21)OCO3]

7) NSC9231: 2,3-Dihydroxypropyl dihydrogen phosphate:

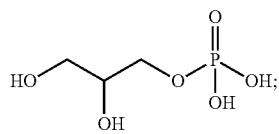

8) NSC16867: 2,3-Dimercaptosuccinic acid:

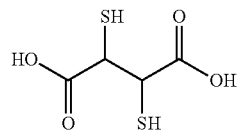

and salts, solvates and hydrates thereof.

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

Methods of synthesizing compounds herein are within the means of chemists of ordinary skill in the art. Methods for optimizing reaction conditions, if necessary minimizing competing by-products, are known in the art. The methods may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

3. USES OF THE COMPOUNDS OF THE INVENTION

In one embodiment, the invention provides methods for treating or preventing neoplasia in a subject, by administering to the subject an effective amount of a compound of the present invention.

In certain embodiments, the methods of the invention include administering to the subject a therapeutically effective amount of a compound of the invention in combination with an additional therapeutic agent. In certain embodiments, the compound of the invention can be used in combination therapy with conventional anti-cancer therapeutics. Some embodiments provide that the additional therapeutic agent is selected from the group consisting of fluorinated pyrimidine fluorouracils and folate analogues. A particular example is that the additional therapeutic agent is 5-fluorouracil.

The additional therapeutic agents can include the following drugs, usually in combinations with each other, that are often used to treat acute leukemias: vincristine, prednisone, methotrexate, mercaptopurine, cyclophosphamide, and cytarabine. Other examples include, for example, doxorubicin, cisplatin, taxol, 5-fluorouracil, etoposid, etc., which demonstrate advantages (e.g., chemosensitization of cells) in combination with the compounds described herein. In chronic leukemia, for example, busulfan, melphalan, and chlorambucil can be used in combination. Proteosome inhibitors (e.g., MG-132), hydroxyureas (e.g., Hydrea or hydroxycarbamide) or kinase inhibitors (e.g., GLEEVEC) can also be used in combination with the compounds of the present invention. Examples of therapeutic agents also include compounds known to treat cancer, e.g., anticancer agents, antitumor agents, antiangiogenesis agents, chemotherapeutics, antibodies, etc. Other therapeutic agents that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the additional therapeutic agent may be administered to the subject in the same pharmaceutical composition or in different pharmaceutical compositions (at the same time or at different times).

Certain embodiments provide that the compound of the present invention and the additional therapeutic agent are administered simultaneously to the subject. Other embodiments provide that the compound of the present invention and the additional therapeutic agent are administered sequentially to the subject being treated.

In other aspects, the invention provides a method of treating a subject suffering from or susceptible to neoplasia, wherein the subject has been identified as in need of treatment for a neoplasia, comprising administering to said subject in need thereof, an effective amount of a compound or pharmaceutical composition herein, such that said subject is treated for said disorder.

Determination of a therapeutically effective amount or a prophylactically effective amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the subject in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific cancer involved; pharmacodynamic characteristics of the particular agent and its mode and route of administration; the desired time course of treatment; the species of mammal; its size, age, and general health; the specific cancer involved; the degree of or involvement or the severity of the cancer; the response of the individual subject; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-cancer amount of a compound of the invention of the invention is expected to vary from about 0.001 mg/kg of body weight per day to about 100 mg/kg/day.

Also, the invention provides the use of a compound of any of the present aspects of the invention herein, alone or together with one or more additional therapeutic agents in the manufacture of a medicament, either as a single composition or as separate dosage forms, for treatment or prevention in a subject of a disease, disorder or symptom set forth herein. Another aspect of the invention is a compound herein for use in the treatment or prevention in a subject of a disease, disorder or symptom thereof delineated herein.

The method of the present invention may further include treating said subject with an additional cancer treatment. Certain embodiments provide that additional cancer treatment is selected from the group of surgery, chemotherapy, radiation therapy, immunotherapy and monoclonal antibody therapy. One embodiment is that the additional cancer treatment is an immunotherapy. Certain embodiments provide that the immunotherapy is individualized, based on the generation of tumor antigen specific T lymphocytes.

Compounds determined to be effective for the prevention or treatment of neoplasia in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

The identification of those subjects who are in need of neoplasia treatment is well within the ability and knowledge of one skilled in the art. Certain of the methods for identification of subjects which are at risk of developing neoplasia which can be treated by the subject method are appreciated in the medical arts, such as family history, and the presence of risk factors associated with the development of that disease state in the subject. A clinician skilled in the art can readily identify such candidate subjects, by the use of, for example, clinical tests, physical examination and medical/family history.

A method of assessing the efficacy of a treatment in a subject includes determining the pre-treatment extent of a cancer by methods well known in the art (e.g., determining tumor size or screening for cancer markers where the cancer is present) and then administering to the subject a therapeutically effective amount of a compound capable of inhibiting the activity of the thymidylate synthetase through interfering with or modulating association among the thymidylate synthetase monomers. After an appropriate period of time after the administration of the compound (e.g., 1 day, 1 week, 2 weeks, one month, six months), the extent of the cancer is determined again. The modulation (e.g., decrease) of the extent or severity of the cancer indicates efficacy of the treatment. The extent or severity of the cancer may be determined periodically throughout treatment. For example, the extent or severity of the cancer may be checked every few hours, days or weeks to assess the further efficacy of the treatment. A decrease in extent or severity of the cancer indicates that the treatment is efficacious. The method described may be used to screen or select subjects that may benefit from treatment with a compound of the present invention.

Yet another aspect provides a method to identify a compound for treating or preventing neoplasia in a subject. The method comprises a) obtaining thymidylate synthases, wherein said thymidylate synthases comprise monomers; and b) evaluating inhibitory activity of said compound against the thymidylate synthases. Some embodiments provide that the method further includes evaluating inhibitory activity of a mixture against the thymidylate synthases, wherein the mixture consists essentially of the compound and an additional anti-cancer agent.

In one embodiment, the method further includes determining whether the compound being evaluated has a non-competitive or competitive inhibitory activity against the thymidylate synthase by comparing the inhibitory activity of the compound with the inhibitory activity of the mixture. In one embodiment, the compound of the methods herein is identified for use herein in the aforementioned manner.

A method of the present invention may also include obtaining or separating thymidylate synthase monomers. The method may also include obtaining the crystal structure of the thymidylate synthase, or specific domains thereof (optionally apo form or complexed) or obtaining the information relating to the crystal structure of thymidylate synthase, or specific domains thereof (optionally apo form or complexed), in the presence and/or absence of the test compound. Certain embodiments include obtaining the crystal structure of a thymidylate synthase monomer.

X-ray crystallography is utilized to characterize the mechanism of action for selecting the thymidylate synthase inhibitors in order to identify one or more specific binding pockets in the thymidylate synthase monomer, wherein the binding pocket plays a role in association among the monomers. Then, compounds are computer-screened for their abilities to interact with the binding pocket in the thymidylate synthase based on the coordinates derived from the enzyme crystal structure. Each compound is molecularly docked and its binding affinity assessed.

In another aspect, the invention provides methods for inhibiting cell proliferation. In one embodiment, a method of inhibiting cell proliferation (or a cancer) according to the invention includes contacting cells with a compound capable of modulating or interfering with association among thymidylate synthase monomers. In one embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of treating or preventing neoplasia by administering to the subject an effective amount of a compound of the present invention. The administration may be by any route of administering known in the pharmaceutical arts.

If the modulation of the enzyme status indicates that the subject may have a favorable clinical response to the treatment, the subject may be treated with the compound. For example, the subject can be administered therapeutically effective dose or doses of the compound.

In certain aspects, the invention provides a method for treating or preventing neoplasia in a subject including assessing the efficacy of the treatment in a subject, monitoring the progress of a subject being treated with a thymidylate synthase modulator (or inhibitor) of the present invention, identifying a subject with neoplasia for treatment with the thymidylate synthase modulator (or inhibitor), and/or treating a subject suffering from or susceptible to neoplasia (e.g., cancer). In certain embodiments, the method of the invention provides using a kit for treating or preventing neoplasia in a subject.

The kit may include a compound of the invention, for example, a compound described herein or pharmaceutically acceptable esters, salts, hydrates, solvates, or prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like. Compounds of the invention can be initially tested in vitro using cells or other mammalian or non-mammalian animal models. Alternatively, the effects of compounds of the invention can be characterized in vivo using animals models.

4. PHARMACEUTICAL COMPOSITIONS

The invention also provides a pharmaceutical composition, comprising an effective amount of a compound of the present invention and/or a pharmaceutically acceptable carrier. In one embodiment, the effective amount is effective to treat or prevent neoplasia in a subject, as described previously.

In another aspect, a compound of the invention is packaged in a therapeutically effective amount with a pharmaceutically acceptable carrier or diluent. The composition may be formulated for treating or preventing neoplasia in a subject, and packaged with instructions to treat a subject suffering from or susceptible to neoplasia.

In an embodiment, the compound of the invention is administered to a subject in need thereof using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compounds of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of 100%, this amount will range from about 1% to about 99% of active ingredient, preferably from about 5% to about 70%, more preferably from about 10% to about 30%.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes.

The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (or 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular subject, composition, and mode of administration, without being toxic to the subject. An exemplary dose range is from about 0.1 to about 10 mg/kg per day.

A preferred dose of the compound of the invention for the present invention is the maximum that a subject can tolerate and not develop serious side effects. Preferably, the compound of the invention of the present invention is administered at a concentration of about 0.001 mg/kg to about 100 mg/kg of body weight, about 0.001-about 10 mg/kg or about 0.1 mg-about 10 mg/kg of body weight. Ranges intermediate to the above-recited values are also intended to be part of the invention.

5. SCREENING METHODS AND SYSTEMS

In another aspect, the invention provides a machine readable storage medium which comprises the structural coordinates of either one or both of the binding pockets identified herein, or similarly shaped, homologous binding pockets in thymidylate synthetase. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which inhibits the activity of thymidylate synthase through modulating or interfering with association among the thymidylate synthase monomers. Thus, the computer produces a three-dimensional graphical structure of a molecule or a molecular complex which comprises a binding pocket in the thymidylate synthase. A particular example is that the computer produces a three-dimensional graphical structure of a molecule or a molecular complex which comprises a binding pocket in the thymidylate synthase monomer.

In another embodiment, the invention provides a computer for producing a three-dimensional representation of a molecule or molecular complex defined by structure coordinates of the thymidylate synthase or domains thereof, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms.

In exemplary embodiments, the computer or computer system can include components which are conventional in the art, e.g., as disclosed in U.S. Pat. Nos. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket in thymidylate synthase may be used for a variety of purposes, such as drug discovery.

For example, the structure encoded by the data may be computationally evaluated for its ability to associate with chemical entities. Chemical entities that associate with the structural pocket of thymidylate synthase which in turn modulates or inhibits association among thymidylate synthase monomers are potential drug candidates. Alternatively, the structure encoded by the data may be displayed in a graphical three-dimensional representation on a computer screen. This allows visual inspection of the structure, as well as visual inspection of the structural pocket's association with chemical entities.

Thus, according to another embodiment, the invention relates to a method for evaluating the potential of a chemical entity to associate with a) a molecule or molecular complex comprising a thymidylate synthase monomer, or specific domains thereof, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding pocket in thymidylate synthase or a complex of the enzyme; and ii) analyzing the results of the fitting operation to quantify the association between the chemical entity and the binding pocket in the thymidylate synthase.

Certain embodiments provide that the afore-mentioned thymidylate synthase is in monomeric form.

The term "chemical entity", as used herein, refers to chemical compounds, complexes of at least two chemical compounds, and fragments of such compounds or complexes.

The design of compounds capable of inhibiting the activity of thymidylate synthase through modulating or interfering with association among thymidylate synthase monomers according to this invention generally involves consideration of several factors. First, the entity must be capable of physically and structurally associating with parts or all of the thymidylate synthase binding sites. Non-covalent molecular interactions important in this association include hydrogen bonding, van der Waals interactions, hydrophobic interactions and electrostatic interactions. Second, the entity must be able to assume a conformation that allows it to associate directly with the binding pocket in a thymidylate synthase monomer. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on thymidylate synthase, or specific domains thereof-related binding pocket may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule to inhibit thymidylate synthase through modulating or interfering with association among the thymidylate synthase monomers, or specific domains thereof activity, e.g., using assays described herein or known in the art. In this manner, synthesis of inoperative compounds may be avoided.

A potential inhibitor of thymidylate synthase which modulates or inhibits association among the thymidylate synthase monomers, or specific domains thereof-related binding pocket may be computationally evaluated by means of a series of steps in which chemical entities or fragments are screened and selected for their ability to inhibit or modulate thymidylate synthase which inhibits or modulates association among the enzymes, or specific domains thereof-related binding pockets.

One skilled in the art may use one of several methods to screen chemical entities or fragments for their ability to inhibit or modulate thymidylate synthase through interfering with or modulating association (or dimerization) of the enzyme, or specific domains thereof-related binding pocket. This process may begin by visual inspection of, for example, thymidylate synthase, or specific domains thereof-related binding pocket on the computer screen based on binding site of a thymidylate synthase, or specific domains thereof structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention [see, e.g., N. C. Cohen et al., "Molecular Modeling Software and Methods for Medicinal Chemistry, J. Med. Chem., 33, pp. 883-894 (1990); see also, M. A. Navia and M. A. Murcko, The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein. Many thousands of compounds can be rapidly screened and the best virtual compounds can be selected for further screening (e.g., by synthesis and in vitro testing). Small molecule databases can be screened for inhibitory activities against thymidylate synthase through modulating or interfering with association (e.g. dimerization) of the enzymes, or binding to the aforementioned binding pocket in the enzyme. In this screening, the quality of fit of such entities to the binding site may be judged either by shape complementarity or by estimated interaction energy.

In certain embodiments, a binding pocket at the dimer interface of TS can be identified using coordinates from the crystal structure of human TS (PDB code 1 HZW).

EXAMPLES

The invention is further illustrated by the following examples which are intended to illustrate but not limit the scope of the invention.

Example 1

Database of Small Molecules

The NCI/DTP databases contain a repository of approximately 240,000 small molecules which are non-proprietary and offered to the research community for discovery and development of new agents for the treatment of cancer, AIDS, or opportunistic infections afflicting subjects with cancer or AIDS.

Example 2

We attempted to identify a "hotspot" at the dimer interface critical for homodimerization and enzymatic activity. In certain embodiments, a binding pocket at the dimer interface of TS can be identified using coordinates from the crystal structure of human TS (PDB code 1HZW). We found that Arg175 contributes more buried surface area at the TS dimer interface than any other residue. We selected a structural pocket at this site with chemical and geometric features compatible with drug binding.

Approximately 140,000 small molecule compounds have been screened for their abilities to interact with a binding pocket in a human thymidylate synthase monomer based on the coordinates derived from the crystal structure (FIG. 1). DOCK (UCSF) and the Docker program have been utilized. The high throughput virtual screening was performed at the High Performance Computing and Simulation Center at the University of Florida using 16 processors on the linux cluster.

The crystal structure of human thymidylate synthase was used as the basis for screening approximately 140,000 drug candidates. The top scoring compounds were obtained and rapidly screened for their abilities to inhibit the biochemical activity of human thymidylate synthase. Through the screening, forty compounds are found to achieve high scores with respect to their abilities to interact with the structural pocket outside the conventional active site on human thymidylate synthase. These compounds were then obtained and tested for their abilities to inhibit the biochemical activity of human thymidylate synthase. The test results are summarized in Table 1:

TABLE 1

| Compound ID | Ki + 0.12 µM | docking score (kcal per mol) |
|---|---|---|
| NSC60718 | 4.41E−05 | −34.7767 |
| NSC49467 | 2.98E−05 | −35.3896 |
| NSC141235 | 1.77E−04 | −40.691574 |
| NSC111180 | 5.40E−06 | −33.4967 |
| NSC86777 | 6.02E−04 | −37.518806 |
| NSC304467 | 3.21E−08 | −45.01368 |
| NSC9231 | 2.12E−06 | −45.714935 |
| NSC16867 | 4.55E−05 | −36.5879 |
| 5-FU | 5.67E−05 | |

Further, the kinetic parameters of thymidylate synthase in presence of the compounds were also measured. The results are presented in Table 2 as follows:

TABLE 2

| Compounds | Hit | Score $\Delta G^a$ (kcal/mol) | XlogP | Ki, µM |
|---|---|---|---|---|
| NSC60718 | #5 | −34.776 | −1.15 | 29.80 |
| NSC49467 | #4 | −35.389 | 1.91 | 177.0 |
| NSC141235 | #12 | −40.691 | — | 5.40 |
| NSC111180 | #11 | −33.497 | −0.66 | 602.0 |
| NSC304467 | #5 | −37.519 | 1.59 | 0.320 |
| NSC9231 | #1 | −45.014 | −1.93 | 2.120 |
| NSC16867 | #2 | −36.590 | −1.01 | 45.50 |
| 5-FU | — | — | — | 56.70 |

Kinetic Parameters of Thymidylate Synthase (TS) in Presence of Selected Compounds The above results have demonstrated that the compounds of the invention inhibit TS activity. In particular, NSC304467 (1-ethyl-4-oxo-1,4-dihydro[1,3]-dioxolo[4,5-g]cinnoline-3-carboxylic acid, also known as cinoxacin or CNX) is potent in inhibiting TS activity. Analysis of the enzyme mechanism suggests that cinoxacin inhibits TS in a non-competitive manner, consistent with the activity of a drug that binds in an allosteric site.

Cell proliferation experiments using HT29, HeLa and several other human cancer cells lines show that combinations of CNX treatment with 5-FU produced greater inhibitory effects than 5FU alone. The combination of certain compounds (e.g., CNX) with certain anti-cancer compounds (e.g., 5-FU) can produce synergistic anticancer effects.

Example 3

Database Screening To Identify Potential Small Molecule Inhibitors of Thymidylate Synthase In lieu of conducting high-throughput screening, a more rapid and economical structure-based approach combining molecular docking in silico with functional testing was used. A large chemical library of compounds with known three-dimensional structure is positioned in the structural pocket of the thymidylate synthase structure (see FIG. 1).

For the model building, the sequence of human thymidylate synthase was used as a template. This is from the PDB database, the PDB code: 1YVJ.

Example 4

Enzyme Assay to Identify Specific Binding Mechanisms for a Thymidylate Synthase Inhibitor Method:

A spectrophotometric assay is used to test compounds for their inhibitory activity against human thymidylate synthase activity. This assay is a modification of the assay of Wahba, A. J., and Friedkin, M. (1961). Direct spectrophotometric evidence for the oxidation of tetrahydrofolate during the enzymatic synthesis of thymidylate (J. Biol. Chem. 236, PC11-12).

In the spectrophotometric assay, human thymidylate synthase is preincubated with deoxyuridine monophosphate (and inhibitors) in 96-well plates for 0-5 minutes at room temperature and fresh 5,10-methylene tetrahydrofolate (THF) is added to the mixture immediately before the reaction to yield a volume of 100 µl. 5,10-methylene tetrahydrofolate is prepared fresh prior to every experiment by dissolving THF in 0.26 M formaldehyde, 80 mM dithiothreitol, and 50 mM Tris HCl (pH 6.8/7.0). X-ray crystallography is then utilized to identify any binding site in human thymidylate synthase for an inhibitor and also to characterize its mechanism of action.

The 40 highest scoring compounds in the above-mentioned screening assay were obtained and tested for their abilities to inhibit the biochemical activity of human thymidylate synthase. Four compounds were inhibitory and preliminary studies show the enzyme mechanism to be non-competitive (i.e. through modulating or interfering with association among human thymidylate synthase monomers). The test results are summarized in Table 1. Certain compounds herein demonstrate synergistic activity in combination with anticancer agents (e.g., 5-FU).

Example 5

This experiment focuses on peptides capable of interacting with the Human Leukocyte Antigen A molecules expressed on a diverse set of cancer cell types. Well-characterized peptide binding motifs for Human Leukocyte Antigen A molecules are used to select peptides derived from human thymidylate synthase to stimulate T lymphocytes isolated from peripheral blood mononuclear cells. The experiment is designed to formulate a rapid and economical protocol to generate tumor specific T cells in an individually optimized manner and boost the adaptive immune response.

Method:

Peripheral blood mononuclear cells are obtained by Ficoll-Hypaque gradient separation of buffy coats of blood samples collected from four different Human Leukocyte Antigen-typed healthy human donors and four colon cancer subjects who gave written informed consent. The dendritic cells used for in vitro cytotoxic T lymphocyte stimulation are generated from autologous peripheral blood mononuclear cells. Cytotoxic T lymphocyte lines are generated from peripheral blood mononuclear cells as previously described in the art.

Peripheral blood mononuclear cells from donors are added to autologous irradiated dendritic cells loaded with peptides corresponding to Human Leukocyte Antigen binding human thymidylate synthase epitopes (25 µg/mL per $10^6$ cells) for 1 hour at a peripheral blood mononuclear cell/dendritic cell ratio of five to one. After a 5-day coculture of peripheral blood mononuclear cells and dendritic cells in the presence of granulocyte-macrophage colony-stimulating factor and interleukin-4, the cells are maintained in complete medium containing 5% human AB (AB blood group) serum and low-dose [(25 U/mL)] interleukin-2 for another 10 days and are then restimulated as described above. After at least four in vitro stimulations, the CTL cultures are evaluated for immunophenotype and cytotoxic activity. All cytotoxic T lymphocyte lines are examined by flow cytometry and, based on previous studies, are expected to show the following immunophenotype: CD3+=90%-95%; CD56+=10%-22%; CD4+=37%-40%; and CD8+=40%-50%.

Patient derived cancer target cells are treated with a sublethal dose of 5-fluorouracil and combinations of selected human thymidylate synthase inhibitors. Tumor cells are seeded at a concentration of $2 \times 10^5$ cells/mL in 25-cm$^2$ flasks (Falcon, Lincoln Park, N.J.). On the third day after seeding, 5-fluorouracil and selected compounds are added to a concentration of $10^{-4}$ M for 1 hour. The drugs are then removed by multiple washings with phosphate-buffered saline, and fresh medium are then added to the cells. Thymidylate synthase expression is evaluated by immunoblotting and by immunocytofluorimetric analysis 6, 24, and 48 hours later by using thymidylate synthase specific monoclonal antibody 4130.

Through this experiment, tumor antigen peptides derived from human thymidylate synthase are rapidly identified and further can be synthesized. These peptides are capable of binding individual forms of Human Leukocyte Antigens. These tumor antigen peptides are expected to stimulate strong cytotoxic T cell responses against colon carcinoma cells in different individuals.

Example 6

Method

Standard Cr$^{51}$ release and established measures of cytotoxicity and proliferation are used to evaluate the combined effects of small molecule and cellular treatments of subject derived colon carcinoma cells.

Through this experiment, a protocol consisting of a cocktail of small molecule inhibitors combined with immunotherapy which stimulates tumor specific adaptive immune responses are identified.

This experiment is to evaluate the combination of direct human thymidylate synthase inhibitors with cytotoxic T lymphocytes specific for Human Leukocyte Antigen restricted epitopes of human thymidylate synthase.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The contents of all references (including literature references, issued patents, published patent applications, and co-pending patent applications) cited throughout this application are hereby expressly incorporated herein in their entireties by reference.

Those skilled in the art will recognize, or be able to ascertain using no more than routine experimentation, many equivalents of the specific embodiments of the invention described herein. Such equivalents are intended with be encompassed by the following claims.

What is claimed is:

1. A method of treating colon cancer in a subject, said method comprising administering to said subject an effective amount of a compound selected from the group consisting of (3,5-diiodo-4-oxo-1(4H)-pyridinyl)acetic acid, P-(diethylsulfamoyl)benzoic acid, 3-(acetylamino)-2,4,6-triiodobenzoic acid, 6-(methylamino)hexane-1,2,3,4,5-pentol, 2-acetamido-3-sulfanylpropanoic acid, Piperazine 2,3-dihydroxysuccinate, 1-ethyl-4-oxo-1,4-dihydro[1,3]dioxolo[4,5-g]cinnoline-3-carboxylic acid, 2,3-dihydroxypropyl dihydrogen phosphate, and 2,3-dimercaptosuccinic acid ("NSC16867"); or a pharmaceutically acceptable salt thereof, wherein said compound is capable of interfering with or modulating association among thymidylate synthase monomers.

2. The method of claim 1, wherein said method comprises administering to said subject an additional therapeutic agent.

3. The method of claim 2, wherein said additional therapeutic agent is selected from the group consisting of fluorinated pyrimidine fluorouracils and folate analogues.

4. The method of claim 3, wherein said additional therapeutic agent is 5-fluorouracil.

5. The method of claim 2, wherein said compound and said additional therapeutic agent are administered simultaneously.

6. The method of claim 2, wherein said compound and said additional therapeutic agent are administered sequentially.

7. The method of claim 1, wherein said method further includes treating said subject with an additional cancer treatment.

8. The method of claim 7, wherein said additional cancer treatment is selected from the group of surgery, chemotherapy, radiation therapy, immunotherapy and monoclonal antibody therapy.

9. The method of claim 8, wherein said additional cancer treatment is an individualized immunotherapy.

10. The method of claim 1, wherein said compound is 1-ethyl-4-oxo-1,4-dihydro[1,3]dioxolo[4,5-g]cinnoline-3-carboxylic acid, or a pharmaceutically acceptable salt thereof.

* * * * *